ary Examiner—Amy B. Vanatta

United States Patent [19]

Sandbank

[11] Patent Number: 5,640,720
[45] Date of Patent: Jun. 24, 1997

[54] MEDICAL APPARATUS

[75] Inventor: Barry Michael Sandbank, Chester, United Kingdom

[73] Assignee: Ansell Perry Inc., Massillon, Ohio

[21] Appl. No.: 424,445

[22] PCT Filed: Oct. 28, 1993

[86] PCT No.: PCT/GB93/02224

§ 371 Date: May 19, 1995

§ 102(e) Date: May 19, 1995

[87] PCT Pub. No.: WO94/09965

PCT Pub. Date: May 11, 1994

[30] Foreign Application Priority Data

Oct. 31, 1992 [GB] United Kingdom ............... 9222865

[51] Int. Cl.⁶ .................... A41D 19/00; B29C 55/00
[52] U.S. Cl. .................... 2/169; 2/168; 264/537; 264/530
[58] Field of Search ................ 264/526, 530, 264/523, 534, 537; 2/169, 168, 163, 161.7; 425/DIG. 44, 543, 573, 522, 525, 529, 530, 538, 533

[56] References Cited

U.S. PATENT DOCUMENTS

| | | | |
|---|---|---|---|
| 2,248,898 | 7/1941 | Ross et al. | 264/523 |
| 3,690,804 | 9/1972 | Nave | 264/98 |
| 4,034,036 | 7/1977 | Farrell | 264/530 |
| 4,050,887 | 9/1977 | Berggren et al. | 264/530 |
| 4,086,314 | 4/1978 | Lampert et al. | 264/526 |
| 4,087,503 | 5/1978 | Peters | 264/526 |
| 4,115,873 | 9/1978 | Stansbury | 2/169 |
| 4,344,749 | 8/1982 | Fritz et al. | 264/530 |
| 4,921,672 | 5/1990 | Bock | 2/169 |
| 4,935,190 | 6/1990 | Tennerstedt | 264/530 |
| 5,002,718 | 3/1991 | Tanaka et al. | 264/530 |
| 5,017,325 | 5/1991 | Jackowski et al. | 264/530 |
| 5,130,159 | 7/1992 | Shienker et al. | 2/168 |
| 5,350,361 | 9/1994 | Tsukashima et al. | 264/523 |
| 5,360,590 | 11/1994 | Wheeler | 264/523 |

FOREIGN PATENT DOCUMENTS

| | | |
|---|---|---|
| 456333 | 11/1991 | European Pat. Off. . |
| 89/11258 | 11/1989 | WIPO . |

Primary Examiner—Amy B. Vanatta
Attorney, Agent, or Firm—Gardner, Carton & Douglas

[57] ABSTRACT

There is disclosed a method of manufacturing flexible elastomeric articles such as gloves, which comprises molding the glove body from a parison of the elastomeric material and stretching the stump portions into finger and thumb portions.

13 Claims, 2 Drawing Sheets

MEDICAL APPARATUS

BACKGROUND OF THE INVENTION

1. Field of the Invention

This invention relates to flexible elastomeric articles, for example, gloves and condoms, processes for their manufacture and formers for use in the manufacturing processes.

2. Scope of the Prior Art

The manufacture of elastomeric gloves by vacuum molding is known from U.S. Pat. No. 3,124,807. The methods described therein comprise the vacuum molding and heat sealing of two sheets of a thermoplastic elastomeric material. However, gloves made from this method will generally possess one or more seams which may be a source of rupture or leakage.

More conventional methods of manufacturing synthetic. elastomeric gloves which overcomes the problem of having seams comprises solvent dipping of an appropriately shaped former into a suitable polymer solvent mix, withdrawing the polymer coated former and then drying off the solvent before stripping the glove therefrom. There are a number of disadvantages with this method, in particular the use of large amounts of solvent is undesirable. Equally, the method of dipping is both time consuming and costly since it is necessary to have a series of formers for dipping which cannot be rapidly reused. Additionally, gloves produced by this method are likely to have residual solvent in them which is toxic and therefore an unacceptable containment.

Blow molding of rigid plastic articles is known, eg. in the manufacture of rigid plastic bottles. However, such techniques have not been used with thin walled flexible elastomeric articles.

WO89/11258 discloses condoms comprising a blow formed tubular main sheath. However, WO89/11258 does not disclose the use of such technology in relation to gloves.

SUMMARY OF THE INVENTION

The present invention seeks to overcome the abovementioned disadvantages by providing flexible elastomeric articles, especially thin walled articles, a method of manufacturing an article body and then stretching the article body in order to produce a flexible elastomeric article.

According to the invention we provide a flexible elastomeric body comprising a flexible elastomeric material the body of which is adapted to be stretched beyond the yield point of the flexible elastomeric material to produce a flexible elastomeric article.

By the term article we include, inter alia, gloves and condoms.

According to a further feature of the invention, we provide a flexible elastomeric body to comprising a glove body comprising hand and cuff portions wherein the finger and thumb portions are stumps which stumps are adapted to be stretched beyond the yield point of the flexible elastomeric material to produce a glove.

With reference to gloves, the finger and thumb stumps may be a stretched by applying stretching means. Such stretching means may be a mechanical means, such as a system of mechanical plungers which stretch the finger and thumb stumps to form the fingers and thumb of the glove, or alternatively a system of clamps which pull the finger and thumb stumps.

Preferably, since the finger and thumb stumps have inner and outer surfaces, they may be stretched by creating a pressure differential between the inner surface and outer surface of the stumps. That is, stretching may be carried out either by applying a pressure, eg. blow molding, to the inner surface, or by applying a vacuum, eg. vacuum molding, to the outer surface of the stumps. It is particularly preferable to apply pressure or vacuum to the glove form.

Conventional molding techniques may be used in the manufacture of the flexible elastomeric body, ie. molding a flexible elastomeric material into an appropriately shaped body. Molding techniques such as blow molding, eg. of a parison of a flexible elastomeric material or injection molding may be used. Conventional conditions known per se could be used in the manufacture of a flexible elastomeric body.

The glove body as hereinbefore described may be manufactured by conventional methods known per se, such as methods described in Handbook of Thermoplastic Elastomers edited by Benjamin M Walker, which is incorporated herein by reference. Preferably the glove body is manufactured by blow molding a parison of plastics material to produce a glove body comprising hand and cuff portions wherein the finger and thumb portions are stumps.

A condom body may be manufactured by techniques analogous to those used for glove manufacture.

In order that the finger and thumb portions of the glove are of smaller thickness to the hand and cuff portions, the finger and thumb stumps body will generally be of at least equal thickness or preferably greater thickness than the remainder of the hand and cuff portions created.

During the stretching, the polymer used to produce the gloves undergoes "strain hardening" (the alignment of the long chains of the polymer), which at a low thickness actually increase the strength of the flexible elastomeric polymer.

Thus, a glove produced using the glove body described may comprise hand and cuff portions of greater thickness than the finger and thumb portions. Preferably the finger and thumb portions are of a thickness less than 50 μm and the remainder of glove body is of a thickness less than 200 μm. As an alternative, the cuff portion may be greater in thickness than the hand portion which will be beneficial in the donning of the gloves as the additional thickness provides additional strength and tear resistance to the glove.

Whereas in the traditional method of manufacturing a glove form the hand and cuff portions may generally be of the same thickness as the finger and thumb stumps, ie. less than 200 μm.

According to yet a further aspect of the present invention there is provided a glove made by the process as hereinbefore described. In particular we provide a glove made from a polyetherester block copolymer such as HYTREL™.

A variety of polymers may be used in the manufacture of the articles and flexible elastomeric bodies of the present invention. The material used in the invention may be any thermoplastic elastomer which material may be stretched beyond their yield value to a point such that the material will be permanently deformed, but at the same time still displays elastic properties in the new deformed state.

According to the invention, we provide a glove as hereinbefore described comprising a thermoplastic elastomer.

By the term thermoplastic elastomer (TPE), we mean compounds which show intermediate behavior between a thermoplastic and an elastomer. They are provided with crosslinks derived from physical means rather than chemical means, as in the case with true rubbers. Consequently, they can be processed as thermoplastics, including, eg. blow molding which is impossible for rubbers. After processing they return to their original state with the crosslinks reforming.

There are a number of different types of TPEs and their distinction is typically made on the method of crosslink. They invariably have a two phase system comprising of rubbery matrix, or sort block embedded in which is a stiff phase comprising a glassy or crystalline polymer, or hard block.

In particular, we prefer thermoplastic elastomers which comprise hard and soft block copolymers, eg. di-block and tri-block copolymers. Typical di- and tri- block copolymers include styrenic di- and tri-block copolymers, eg. styrene-butadiene-styrene and styrene-ethylenebutadiene-styrene. Preferred polymers of this type include those sold by Shell in the UK under the names KRATON and CARIFLEX (Trade Marks).

Other preferred thermoplastic elastomers include polyurethanes where a polyol comprises the soft block and a polyester or polyether glycol the hard block. Polyether polyurethanes are preferred since they tend to be more flexible. Specifically preferred polyurethanes include those available in the UK, ELASTOLLAN (Trade Mark) from BASF, ESTANE (Trade Mark) from BF Goodrich and AVALON (Trade Mark) from ICI.

Thermoplastic polyetheresters may also be mentioned. Such copolymers comprise a polyether soft block and a polyester hard block. Preferred polyetheresters include HYTREL (Trade Mark) available from Du Pont.

In addition to hard and soft block copolymers, thermoplastics for use in the present invention include alloys and blends. For example, blends of polyurethane and vinyl acetate which are polymerised, eg. having a vinyl acetate content of from 10–30% w/w, may be used. Other materials include blends such as polyurethane/high impact polystyrene (PU/HIPS) and EVA/HIPS, copolyamides, eg. polyether block amides, and silicones.

Thus, in particular, hard and soft block copolymers may include those where the soft block may be selected from dienes, eg. alkyldienes such as butadienes, polyols, such as polyether or polyester polyols, polyethers, and vinyl acetates. The hard blocks may be selected from styrenes, glycols, polyesters and polyethylenes.

According to the invention we provide the use of a polymer or polymer blend as hereinbefore defined in the manufacture of a flexible elastomeric article body, or a glove, according to the invention.

According to the invention, we also provide the use of a polyetherester in the manufacture of an article, such as a glove.

The mold for use in the manufacture of the glove form according to the invention is also novel per se. Thus, according to yet a further aspect of the present invention there is provided a mold adapted for use in the production of a blow molded glove form which mold has internal dimensions in the form of glove, hand and cuff portions and with chambers for fingers and thumb stumps.

The mold as hereinbefore described preferably comprises two portions which may be separated to facilitate removal of the glove form.

Further, there is provided a second mold adapted to receive a glove body comprising a hand and cuff portion and finger and thumb stumps which second mold is provided with finger and thumb shaped chambers adapted to correspond with the finger and thumb stumps in the glove. The finger and thumb chambers also optionally are provided at the end distal from the hand portion with conduits for the evacuation of the finger and thumb chambers.

Preferably, the mold is a hollow mold in two parts in the shape of a glove body with finger and thumb stumps. Advantageously, a second hollow mold is provided in the form of a complete glove with finger cavities in order that a glove produced in the first mold may subsequently be stretched into a complete glove in this second mold.

The invention will now be described, but in no way limited, by way of example, with reference to the accompanying drawings.

DETAILED DESCRIPTION OF THE INVENTION

Figure 1:
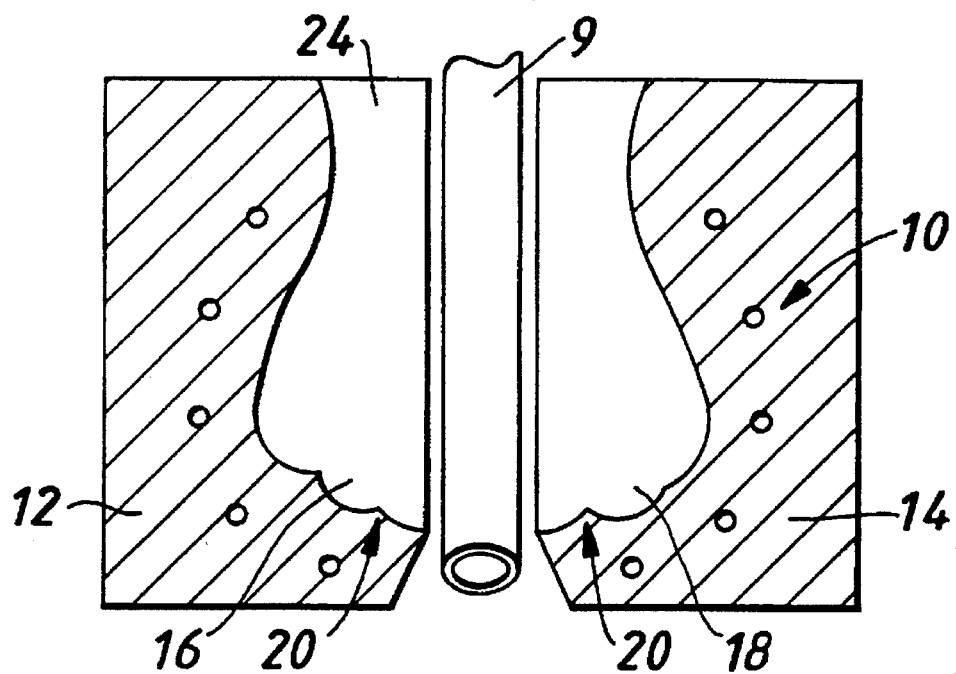
FIG. 1 is a sectional view of a mold for the manufacture of a glove form as hereinbefore described.
Figure 2:
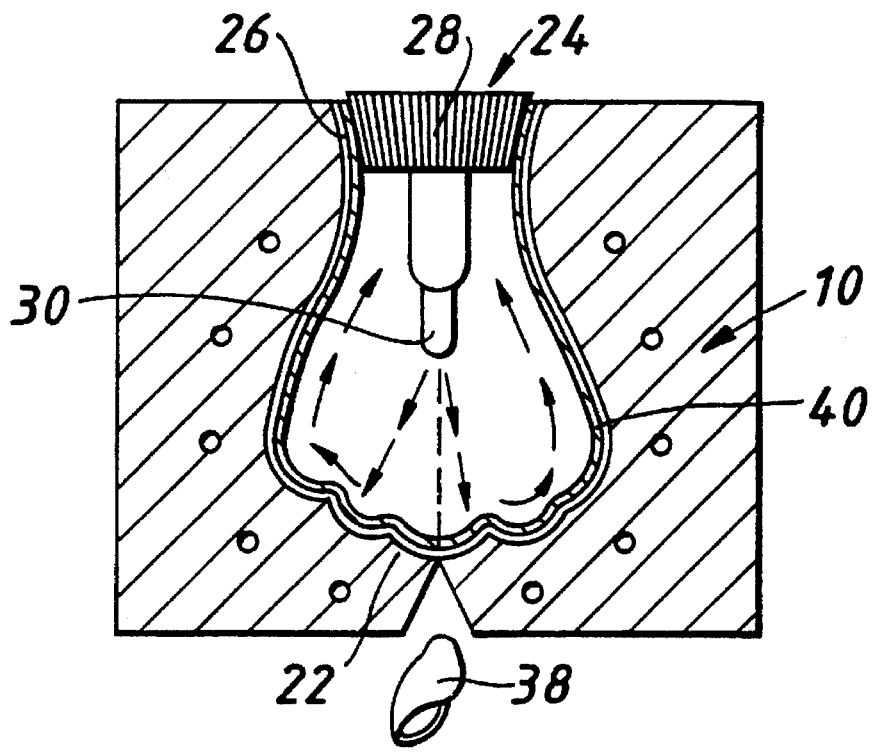
FIG. 2 is a sectional view of the mold of FIG. 1 illustrating the blow mold of a glove body.

Referring to FIGS. 1 and 2, there is illustrated a hollow mold generally designated 10, which hollow mold 10 comprises two halves 12 and 14 respectively. There is also shown in position between the two halves 12 and 14 a parison 9. Each half 12, 14 of the mold 10 is internally shaped in the form of two halves of a glove having internal walls 16 and 18 and having finger and thumb stump chambers generally designated 20.

The two halves 12 and 14 co-operate with each other in such a manner that in union the walls 16 and 18 of the mold form a space defining a glove body 22, with an opening 24 providing a cuff portion 26 to the glove. A parison transport mounting 28 into which a blowing pin 30 is fitted co-operates with the opening 24 and acts as a seal.

In use, a molten parison tube 9, eg. of polyetherester block copolymer such as HYTREL™ is placed between the two halves 12 and 14 of the hollow mold 10. The parison tube 9 is produced by a conventional method of pin extrusion known in the field of blow molding. Once the parison tube 9 is in position and mounted around the parison transport mounting 28, the two halves of the mold 12 and 14 are clamped together to form a space defining the glove body chamber. As a consequence of the two halves 12 and 14 engaging and being clamped, the parison tube 9 is sealed and the waste end of the parison 38 of the tube trimmed away. The blow pin 30 is then placed into the transport mounting 28 and air is injected into the parison tube 9 which expands until it comes into contact with walls 16 and 18 of the hollow mold 10 takes the shape of glove form chamber 21. The mold 10 can then be opened to remove the glove body 40.

Figure 3:
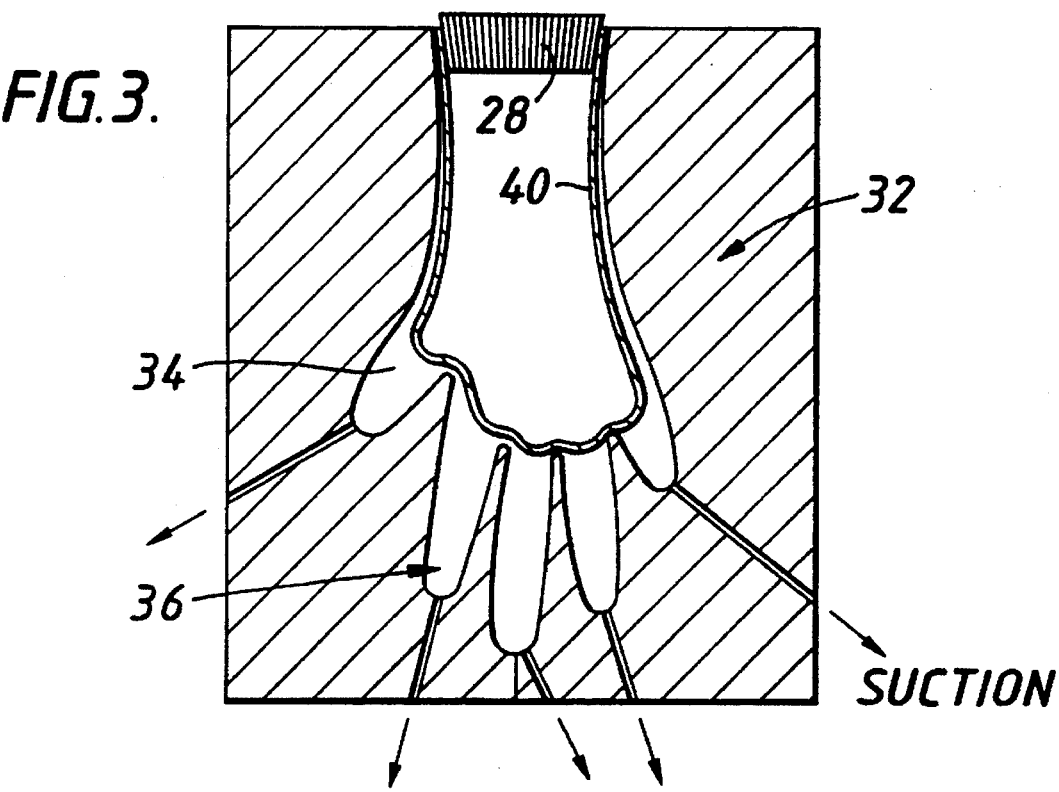
FIG. 3 is a sectional view of a mold for the manufacture of a glove as hereinbefore described illustrating a glove body in position ready to be stretched.

FIG. 3 illustrates a second hollow mold 32 in the form of a complete glove 34 with finger and thumb cavities generally designated 36. The finger and thumb cavities 36 of the glove 34 has its tip remote from the glove body 40 and conduits 39 which form a connection between the fingers 36 of the mold 32 and a means of suction (not illustrated).

The glove body 40 which is still mounted on the transport mounting 28 and which still contains the air injected into it, is then placed in the second hollow mold 32. In position in the mold 32 each of the protrusions 20 correspond with a respective finger cavity 36. In this cold state each of the protrusions 20 are stretched by the use of suction into their respective finger cavities 36. Each protrusion 20 is stretched to a point where the polymer such as HYTREL exhibits a yielding phenomenon whereby the polymer is permanently deformed, but still displays elastic properties in the new deformed state.

Figure 4:
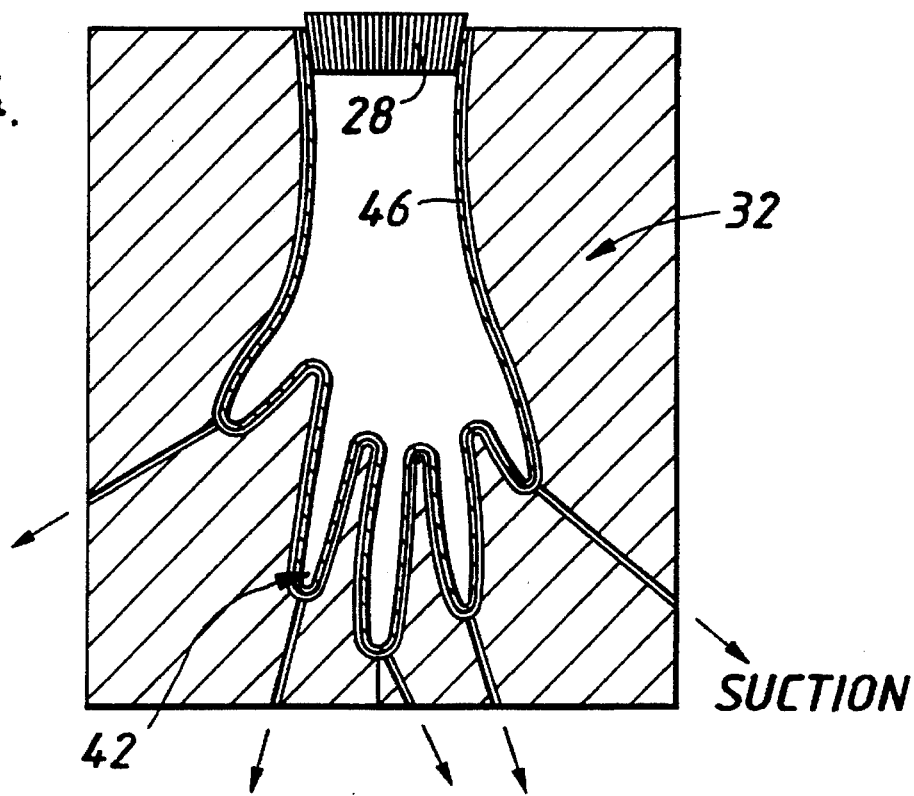
FIG. 4 is a sectional view of a glove after stretching of the glove body within the mold shown in FIG. 3.

Referring to FIG. 4, as a result of the suction applied to the finger and thumb stumps are formed. During the stretching, the polymer used to produce the gloves undergoes "strain hardening" (the alignment of the long chains of the polymer), which at a low thickness actually increase the strength of the polymer.

Having stretched the finger and thumb stumps as illustrated in FIG. 3 and 4 a glove 46 is produced which can then be released from the mold 32.

I claim:

1. A method of manufacturing a glove having a flexible elastomeric body including the steps of:

molding a first glove body from a parison of the flexible elastomeric material using blow injection, wherein the first glove body has a hand portion, a cuff portion, and multiple stump portions, wherein the stump portions can be stretched beyond the yield point of the elastomeric material; and molding a second glove body from the first glove body by molding the stump portions into finger and thumb portions of the glove by stretching the stumps beyond the yield point of the elastomeric material.

2. The method of manufacturing a glove according to claim 1 wherein the molding a first glove body step uses a mold having two halves that come together to form the hand, cuff and stump portions.

3. The method of manufacturing a glove according to claim 1 wherein the molding a second glove body uses a mold having the shape of the glove having the hand, cuff, finger and thumb portions of the glove.

4. The method of manufacturing a glove according to claim 1 wherein the hand and cuff portions of the first glove body have substantially the same thickness as the stumps.

5. The method of manufacturing a glove according to claim 1 wherein the flexible elastomeric material is a thermoplastic elastomer.

6. The method of manufacturing a glove according to claim 1 wherein a pressure differential is created between the inner and outer surface of the stump portions.

7. A method of manufacturing a glove according to claim 6 wherein the pressure differential is created during the second molding step by applying a vacuum to the outer surface of the stumps to form the finger and thumb portions.

8. A method of manufacturing a glove according to claim 1 wherein the finger and thumb portions are made using blow molding techniques.

9. The method of manufacturing a glove according to claim 1 wherein the molding a second glove body includes a stretching means to form the finger and thumb portions from the stumps.

10. A glove made by the method of manufacture according to claim 1 wherein the elastomeric material of the hand and cuff portions are thicker than finger and thumb portions.

11. A glove made by the method of manufacture according to claim 1 wherein the cuff hand portions have a thickness of less than 200 μm.

12. A glove made by the method of manufacture according to claim 1 wherein the finger and thumb portions have a thickness of less than 50 μm.

13. A glove made by the methods of manufacture according to claim 1 wherein the flexible elastomeric material is a polyetherester block copolymer.

* * * * *